United States Patent [19]

Sakimae et al.

[11] Patent Number: 4,629,701
[45] Date of Patent: Dec. 16, 1986

[54] PROCESS FOR PREPARING OPTICALLY ACTIVE CARBOXYLIC ACIDS AND ANTIPODE ESTERS THEREOF

[75] Inventors: Akihiro Sakimae, Ohtake; Yuri Kagawa, Hiroshima; Ryozo Numazawa, Ohtake; Hisao Onishi, Hiroshima, all of Japan

[73] Assignee: Mitsubishi Rayon Company, Limited, Tokyo, Japan

[21] Appl. No.: 627,093

[22] Filed: Jul. 2, 1984

[30] Foreign Application Priority Data

| Jul. 4, 1983 | [JP] | Japan | 58-120281 |
| Jul. 4, 1983 | [JP] | Japan | 58-120282 |
| Aug. 1, 1983 | [JP] | Japan | 58-139478 |
| Oct. 27, 1983 | [JP] | Japan | 58-199943 |
| Dec. 28, 1983 | [JP] | Japan | 58-245784 |

[51] Int. Cl.$^4$ .................. C12P 11/00; C07P 41/00
[52] U.S. Cl. .................. 435/130; 435/280
[58] Field of Search .................. 435/130, 280

[56] References Cited

U.S. PATENT DOCUMENTS

| 4,094,741 | 6/1978 | Yamada et al. | 195/29 |
| 4,452,897 | 6/1984 | Umezawa et al. | 435/280 |

FOREIGN PATENT DOCUMENTS

| 0130752 | 1/1985 | European Pat. Off. | 435/130 |
| 0066493 | 6/1978 | Japan | 435/280 |

Primary Examiner—Jerome D. Goldberg
Assistant Examiner—Joseph A. Lipovsky
Attorney, Agent, or Firm—Oblon, Fisher, Spivak, McClelland, & Maier

[57] ABSTRACT

Organic carboxylic acid ester represented by the formula (II):

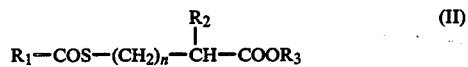

wherein $R_1$ is an alkyl, an aralkyl or an aryl group; $R_2$ is an alkyl group; $R_3$ is an alkyl group; n is 1 or 2, are synthesized in racemic form, and then the acid ester (II) is treated with a source containing enzyme capable of rearranging with or without asymmetrically hydrolyzing ester bond until either a d-form or l-form optically active carboxylic acid ester represented by the formula (II) with or without the antipode acid thereof is produced.

7 Claims, No Drawings

PROCESS FOR PREPARING OPTICALLY ACTIVE CARBOXYLIC ACIDS AND ANTIPODE ESTERS THEREOF

The present invention relates to a process for preparing optically active carboxylic acids represented by the formula:

$$R_1-COS-(CH_2)_n-\underset{\underset{R_2}{|}}{CH}-COOH \qquad (I)$$

wherein $R_1$ is an alkyl group, preferably $C_{1-6}$ alkyl group, an aralkyl group, preferably $C_{7-18}$ aralkyl group or an aryl group, preferably $C_{6-26}$ aryl group; $R_2$ is an alkyl group, preferably $C_{1-6}$ alkyl group; n is 1 or 2, and/or antipode esters thereof.

Optically active carboxylic acids represented by the formula (I) above or esters thereof are utilized as intermediates for the synthesis of various physiologically active materials having optical activity.

Heretofore, processes for preparing the optically active carboxylic acid represented by the formula (I) are known wherein the corresponding racemic carboxylic acid is preliminarily synthesized by organic methods, and the acid is resolved by using various optically resolving agents, that is, an optically active material is physicochemically separated from the antipode thereof (Japanese Published Unexamined Patent Application Nos. 118455/1980, 81557/1981 and 188563/1982, and European Patent Publication No. 79200477).

However, these processes are not always satisfactory as industrial ones. They have such difficulties that a large amount of an expensive resolving agent is required, the resolving agent is liable to be left unremoved as an impurity in the product and the resolving step is very complicated.

The present inventors have been studying a process to asymmetrically hydrolyze these kinds of carboxylic acid esters (II) hereinafter mentioned to find that the optically active carboxylic acid represented by the formula (I) can be prepared in a high efficiency by using source-containing enzyme capable of asymmetrically hydrolyzing esters.

According to the present invention, a process for preparing the optically active carboxylic acid given hereinunder (hereinafter called as the first process) is provided, the carboxylic acid being represented by the formula:

$$R_1-COS-(CH_2)_n-\underset{\underset{R_2}{|}}{CH}-COOH \qquad (I)$$

wherein $R_1$ is an alkyl group, preferably $C_{1-6}$ alkyl group, an aralkyl group, preferably $C_{7-18}$ aralkyl group or an aryl group, preferably $C_{6-26}$ aryl group; $R_2$ is an alkyl group, preferably $C_{1-6}$ alkyl group; and n is 1 or 2, by allowing a source containing enzyme capable of asymmetrically hydrolyzing ester to act on the ester represented by the formula:

$$R_1-COS-(CH_2)_n-\underset{\underset{R_2}{|}}{CH}-COO-R_3 \qquad (II)$$

wherein $R_1$, $R_2$ and n have the same meanings as those mentioned above; and $R_3$ is an alkyl group, preferably $C_{1-6}$ alkyl group.

Furthermore, the present inventors have also studied a modified process (hereinafter called as the second process) to rearrange with or without selectively, asymmetrically hydrolyze either d-form or l-form of the carboxylic acid ester (II) in a mixture thereof. As a result, they find that either d or l form carboxylic acid ester (II) can be prepared in a high efficiency by using an enzyme such as lipase and esterase or a source containing enzyme which is originated from microorganisms such as genuses Aspergillus, Bacillus, Torulopsis and Pseudomonas.

According to the second process, either d or l form carboxylic acid ester (II) is obtained by allowing the specific source containing enzyme capable of rearranging the carboxylic acid ester (II). In this case, the antipode and acid thereof (I) are also produced when the source-containing enzyme is also capable of asymmetrically hydrolyzing ester bond.

In the compounds represented by the formulas (I) and (II), the substituent group $R_1$ is, alkyl group, for example, methyl group, ethyl group or the like; aralkyl group, for example, benzyl group; and aryl group, for example, phenyl group. The substituent groups $R_2$ and $R_3$ are alkyl group, for example, methyl group, ethyl group and the like.

As the starting ester (II) used in the present invention, there can be illustrated, for example, methyl S-acetyl-β-mercaptoisobutyrate, methyl S-acetyl-γ-mercapto-α-methyl-n-butyrate, methyl S-phenylacetyl-β-mercaptoisobutyrate; methyl S-benzoyl-β-mercaptoisobutyrate or the like.

The hydrolyzing enzyme used in the first process of the present invention is a generic name of enzymes capable of asymmetrically hydrolyzing ester bond of the compound (II) mentioned above. In addition to a group of enzymes usually called esterase and lipase, enzymes classified into protease such as, for example, α-chymotripsin can be used for the present invention when they have a capability to hydrolyze the ester. Further, these ester-hydrolyzing enzymes are not limited by their origin, purity and the like, and may be homogenate of animals and plants, cells of microorganisms, and crushed cells and extract of cells.

As microorganisms above to produce these enzymes, there can be illustrated those, for example, belonging to genuses Mucor, Escherichia, Staphylococcus, Agrobacterium, Rhizopus, Aspergillus, Nocardia, Streptomyces, Trichoderma, Candida, Rhodotorula, Torulopsis, Bacillus, Alcaligenes, Pseudomonas, Brevibacterium, Enterobacter, Chromobacterium, Arthrobacter, Microbacterium, Mycobacterium, Saccharomyces, Penicillium, Botrytis, Chaetomium, Ophiobolus, Cladosporium and the like.

As examples of enzymes derived from these microorganisms above sold on the market, there can be illustrated lipase from the genus Mucor (Lipase M-AP 10, manufactured by Amano Pharmaceutical Co.), lipase from the genus Aspergillus (Lipase AP, manufactured by Amano Pharmaceutical Co.), lipase from the genus Candida (manufactured by Sigma Co.), lipase from the genus Rhizopus (Lipase Saiken, Osaka IFO) and the like. Also as enzymes derived from animal tissue, there can be illustrated esterase from pig liver, α-chymotripsin and pancreatin from pancreas and the like.

As microorganisms above, there can be used, for example, Pseudomonas fluorescens, Pseudomonas putida, Pseudomonas ovalis, Escherichia coli, Staphylococcus aureus, Alcaligenes faecalis, Sterptomyces griseus, Streptomyces clavuligerus, Nocardia erthropolis, Nocardia asteraides, Mycobacterium phlei, Agrobacterium radiobacter and the like.

(A) In cases where an enzyme above is used, the reaction is conducted by adding an enzyme and ester to a reaction medium. As the reaction medium, for example, there can be used ion-exchange water or buffer solution containing an inorganic salt such as sodium phosphate and/or an organic salt such as sodium acetate. In order to improve the solubility of the ester, an organic solvent, for example, such as methanol or acetone may be added to the reaction liquid. Though an ester-hydrolyzing enzyme is usually used as it is, an immobilized enzyme may be used. The concentration of ester in the reaction medium is preferably 0.01–50%. Ester may be added batchwise or continuously in the course of the reaction. In this case, also ester in a state of suspension in water may be added.

The pH of the reaction liquid is in a range of 2–11, preferably 5–8. When the pH of the reaction liquid is lowered due to carboxylic acid produced as the reaction proceeds, it is preferable to keep the optimum pH by adding neutralizing agent. The reaction temperature is 5°–50° C. and the reaction time can be appropriately varied depending upon the amount of used enzyme.

(B) In cases where microorganisms are used, the culture of these microorganisms is usually conducted in a form of culture liquid, however, it can be conducted in a form of solid culture. As the culture medium is used one wherein components such as carbon source, nitrogen source, vitamines, minerals and the like which microorganisms can usually assimilate are appropriately combined. In order to increase the hydrolysis capability of microorganisms, addition of a small amount of ester to the culture medium is preferable. The culture is conducted at a temperature of 10°–50° C. and in a pH range of 2–11, preferably 5–8. Aeration and agitation may be conducted to promote the growth of microorganisms.

When the hydrolysis reaction is conducted, ester may be added to the culture medium at the beginning or in the course of culture, or ester may be added to the cultured liquid after microorganisms have been cultivated beforehand. Also cells of propagated microorganisms are collected by centrifugation or other means, and this may be added to the reaction medium containing ester. In this case, for the convenience of handling, dried cells, for example, lyophilized cells, spray-dried cells, cells treated with an organic solvent such as, for example, acetone or toluene, or treated cells such as crushed cells or extract of cells may be used. pH of the reaction liquid varies due to carboxylic acid and the like produced as the reaction proceeds. In this case, it is preferable to maintain the optimum pH by using a suitable neutralizing agent. The concentration of ester in the reaction liquid is preferably 0.01–50% by weight. Also it is preferable to continue the reaction till either d-form or l-form ester is completely hydrolyzed.

The separation and purification of the product from the reaction liquid can be conducted by common methods, for example, means such as extraction, recrystallization and column chromatography.

In the second process, the same enzymes and microorganisms as mentioned above are employed.

In Examples, % means weight percent.

EXAMPLES 1-5

To 50 ml of M/10 phosphate buffer solution (pH 7.0) were added 10 g of (±) methyl S-acetyl-$\beta$-mercaptoisobutyrate and 100 mg of an enzyme described in the table mentioned below, and the mixture was allowed to react by shaking at 30° C. After the reaction over 24 hours, pH of the reaction liquid was adjusted to 7.0, and methyl S-acetyl-$\beta$-mercaptoisobutyrate was removed by extraction with equal volume of ethyl acetate. Then, after pH of the reaction liquid was adjusted to 2.0, S-acetyl-$\beta$-mercaptoisobutyric acid was extracted with equal volume of ethyl acetate. This extract was concentrated to obtain an oily material. This oily material was loaded to silica gel column chromatography adjusted with benzene. By conducting elution while increasing the mixing ratio of acetone to benzene, S-acetyl-$\beta$-mercaptoisobutyric acid was fractioned. When the solvent was removed from this fractioned liquid by evaporation, purified S-acetyl-$\beta$-marcaptoisobutyric acid was obtained. The specific rotatory power of this purified material was measured by using a digital automatic optical rotatory meter (type PM 101) manufactured by Union Giken Co. The results were shown in Table 1.

TABLE 1

| Example No. | Name of enzyme (origin) | Specific rotatory power of S—acetyl-$\beta$-mercaptoisobutyric acid $[\alpha]_D^{20}$: in ethyl acetate |
|---|---|---|
| 1 | α-chymotrypsin (pig pancreas) (Nagase Seikagaku Co.) | +40.8° |
| 2 | esterase (pig liver) Sigma Co.) | +29.5° |
| 3 | lipase (Candida cylindracea) (Sigma Co.) | +35.6° |
| 4 | lipase M-AP10 (genus Mucor) (Amano Pharmaceutical Co.) | −40.6° |
| 5 | pancreatin (pig pancreas) (Nakarai Chemical Co.) | +37.0° |

EXAMPLE 6

Torulopsis gropengiesseri IFO 0659 was inoculated in 100 ml of liquid culture medium (pH 6.0) containing 1.0% of glucose, 0.3% of malt extract, 0.3% of yeast extract and 0.5% of peptone. Shaking culture was conducted at 30° C. for 2 days. After completion of the culture, the cultured liquid was separated by centrifugation. After washing cells obtained (0.4 g in dry basis) with ion-exchange water, they were suspended in 50 ml of M/10 phosphate buffer solution (pH 7.0). To this cell suspension was added 1.0 ml of (±) methyl S-acetyl-$\beta$-mercaptoisobutyrate, and the mixture was allowed to react by shaking at 30° C. for 24 hours.

After adjusting pH of the reaction liquid to 7.0, methyl S-acetyl-$\beta$-mercaptoisobutyrate which did not react was removed by extraction with ethyl acetate. Then, after lowering pH of the water layer to 2.0 with sulfuric acid, S-acetyl-$\beta$-mercaptoisobutyric acid in the water layer was extracted with ethyl acetate. After conducting dehydration treatment of the extract by adding anhydrous sodium sulfate to the extract, the solvent was removed by evaporation to obtain 0.25 g of an oily material. This oily material was loaded to silica gel column adjusted with benzene and eluted with benzene/acetone (10:1) mixture. The elusion region of S-acetyl-β-mercaptoisobutyric acid was fractioned, and the solvent was removed under reduced pressure to obtain 0.19 g of purified S-acetyl-β-mercaptoisobutyric acid. The optical rotation of this purified material was measured and found to be $[\alpha]_D^{25} = -45.0°$ (C=1.1 ethyl acetate).

EXAMPLE 7

*Bacillus subtilis var niger* IFO 3108 was inoculated in 100 ml of liquid culture medium (pH 7.0) containing 1.0% of meat extract, 1.0% of peptone and 0.5% of NaCl. Shaking culture was conducted at 30° C. for 1 day. In the same manner as in Example 1, 0.3 g of washed cells were prepared, the reaction was conducted similarly, the extraction was conducted with ethyl acetate, and finally the column chromatography was conducted to obtain 0.16 g of S-acetyl-β-mercaptoisobutyric acid having $[\alpha]_D^{25} = +42.8°$ (c=1.4 ethyl acetate).

EXAMPLES 8-15

A strain shown in Table 2 was inoculated in 100 ml of liquid culture medium having the same composition as that in Example 6, and shaking culture was conducted at 30° C. for 2-3 days. After separating cells from the cultured liquid and sufficiently washing cells with ion-exchange water, cells were suspended in 50 ml of M/10 phosphate buffer solution containing 1.0 ml of (±) methyl S-acetyl-β-mercaptoisobutyrate. The reaction was conducted at 30° C. for 24 hours. After adjusting pH of the reaction liquid to 7.0, methyl S-acetyl-β-mercaptoisobutyrate was removed by extraction with equal volume of ethyl acetate (neutral extracted fraction). Then, after adjusting pH of water layer of the residual extract to 2.0 or lower, S-acetyl-β-mercaptoisobutyric acid was extracted with equal volume of ethyl acetate (acidic extracted fraction).

The optical rotatory powers of the neutral and acidic extracted fractions were measured with an optical rotatory meter (digital automatic optical rotatory meter Type PM 101, manufactured by Union Giken Co.) respectively to obtain the results shown in Table 2. From these results, it was estimated that strains shown in Table 2 produced optically active S-acetyl-β-mercaptoisobutyric acid having either (+) or (−) optical rotation, and the antipode ester thereof, that is, methyl S-acetyl-β-mercaptoisobutyrate.

TABLE 2

| Example No. | Strain | Optical rotation | |
|---|---|---|---|
| | | Neutral extracted fraction (containing methyl S-acetyl-β-mercaptoisobutyrate) | Acidic extracted fraction (containing S-acetyl-β-mercaptoisobutyric acid) |
| 8 | Aspergillus sojae IAM 2703 | + | − |
| 9 | Candida rugosa IFO 0750 | − | + |
| 10 | Candida parapsilosis IFO 0708 | + | − |
| 11 | Candida utilis IFO 0396 | − | + |
| 12 | Botrytis cinerea IAM 5126 | − | + |
| 13 | Ophiobolus miyabeanus IAM 8053 | − | + |
| 14 | Chaetomium semispirale IFO 8363 | − | + |
| 15 | Cladoporium resinae f. avellaneum HUT 5050 | − | + |

EXAMPLES 16-20

A strain shown in Table 3 was inoculated in 100 ml of liquid culture medium (pH 7.0) containing 1.0% of meat extract, 1.0% of peptone and 0.5% of sodium chloride, and shaking culture was conducted at 30° C. for 1 day. After collecting cells from the cultured liquid by centrifugal separation, cells were washed with ion-exchange water. This washed cells were suspended in 50 ml of M/10 phosphate buffer solution (pH 7.0). To this was added 1.0 ml of (±) methyl S-acetyl-β-mercaptoisobutyrate, and the mixture was shaken at 30° C. for 24 hours. After completion of the reaction, pH of the reaction liquid was adjusted to 7.0, and methyl S-acetyl-β-mercaptoisobutyrate was removed by extraction with ethyl acetate. Then, after lowering pH of water layer of the residual extract to 2.0 or lower with sulfuric acid, S-acetyl-β-mercaptoisobutyric acid was extracted with ethyl acetate. The extract was concentrated to obtain an oily material. This was loaded to silica gel column (Wakogel Q-50, manufactured by Wako Junyaku Co.) adjusted with benzene and eluted with benzene/acetone (4:1) mixture. The elution region of S-acetyl-β-mercaptoisobutyric acid was fractioned, and the solvent was removed under reduced pressure to obtain purified S-acetyl-β-mercaptoisobutyric acid. After dissolving this material in chloroform, the optical rotation was measured with a digital automatic optical rotatory meter (Type PM 101) manufactured by Union Giken Co. The results were as shown in Table 3.

TABLE 3

| Example No. | Name of strain | Hydrolysis percentage (%) | S—acetyl-β-mercaptoisobutyric acid Yield of purified product (g) | Specific rotatory power $[\alpha]_D^{25}$ in chloroform |
|---|---|---|---|---|
| 16 | Pseudomonas ovalis IAM 1049 | 32 | 0.32 | −42.5° |
| 17 | Pseudomonas ovalis IAM 1153 | 30 | 0.19 | −41.8° |
| 18 | Pseudomonas putida IFO 12996 | 45 | 0.30 | −40.9° |
| 19 | Pseudomonas fluorescens IFO 3081 | 50 | 0.42 | −43.5° |
| 20 | Alcaligenes faecalis IFO 13111 | 42 | 0.35 | +40.5° |

EXAMPLES 21–30

Strains in Examples 21–24 were inoculated in the same liquid culture medium as that in Example 16 and strains in Examples 25–30 were inoculated in a liquid culture medium (pH 7.2) containing 1.0% of glucose, 0.2% of peptone, 0.1% of meat extract and 0.1% of yeast extract, respectively. Shaking culture was conducted at 30° C. for 1–3 days. Then, cells were collected from the cultured liquid. After sufficiently washing with ion-exchange water, cells were suspended in 50 ml of M/10 phosphate buffer solution containing 1.0 ml of (±) methyl-S-acetyl-β-mercaptoisobutyrate. The reaction was conducted at 30° C. for 24 hours. Then, after adjusting pH of the reaction liquid to 7.0, methyl S-acetyl-β-mercaptoisobutyrate which did not react was extracted with equal volume of ethyl acetate (neutral extracted fraction). Then, after adjusting pH of water layer of the residual extract to 2.0 or lower, S-acetyl-β-mercaptoisobutyric acid was extracted with equal volume of ethyl acetate (acidic extracted fraction). The optical rotatory powers of neutral and acidic extracted fractions were measured with an optical rotatory meter, and the results were shown in Table 4. From these results, it was estimated that these strains produced optically active S-acetyl-β-mercaptoisobutyric acid having either (+) or (−) optical rotation and the antipode ester thereof, that is, methyl S-acetyl-β-mercaptoisobutyrate.

TABLE 4

| Example No. | Name of strain | Optical rotation Neutral extracted fraction | Optical rotation Acidic extracted fraction |
|---|---|---|---|
| 21 | Escherichia coli IFO 13500 | − | + |
| 22 | Staphylococcus aureus IFO 12732 | − | + |
| 23 | Pseudomonas putida IFO 3738 | + | − |
| 24 | Streptomyces griseus IFO 3355 | − | + |
| 25 | Nocardia erythropolis IFO 12538 | − | + |
| 26 | Nocardia erythropolis IFO 12540 | − | + |
| 27 | Nocardia erythropolis IFO 12539 | − | + |
| 28 | Nocardia asteroides IFO 3384 | − | + |
| 29 | Mycobacterium phlei IFO 13160 | − | + |
| 30 | Streptomyces clavuligerus IFO 13307 | − | + |

EXAMPLE 31

*Agrobacterium radiobacter* IFO 12607 was inoculated in 100 ml of liquid culture medium (pH 7.2) containing 1.0% of meat extract, 0.5% at Nacl and 1.0% of peptone, and shaking culture was conducted at 30° C. for 1 day. After completion of the culture, the cultured liquid was separated by centrifugation. After the total amount of cells obtained was washed with ion-exchange water, cells were suspended in 50 ml of M/10 phosphate buffer solution (pH 7.0). To this cell suspension was added 2.5 ml of (±) methyl S-acetyl-β-mercaptoisobutyrate, and the mixture was allowed to react at 30° C. for 48 hours by shaking.

The decomposition ratio of methyl S-acetyl-β-mercaptoisobutyrate at this time was 49%. After adjusting pH of the reaction liquid to 7.0, methyl S-acetyl-β-mercaptoisobutyrate was extracted with ethyl acetate. Then, after lowering pH of the water layer to 2.0 with sulfuric acid, S-acetyl-β-mercaptoisobutyric acid in the water layer was extracted with ethyl acetate. After conducting dehydration treatment by adding anhydrous sodium sulfate to the extract, the solvent was removed by evaporation. Specific rotatory powers of S-acetyl-β-mercaptoisobutyric acid and methyl S-acetyl-β-mercaptoisobutyrate extracted were measured with an optical rotatory meter (type PM 101) manufactured by Union Giken Co. The results were shown in Table 5.

From these results, it was found that an optically active carboxylic acid and the antipode ester thereof were produced.

TABLE 5

| Reaction product | Specific rotatory power $[\alpha]_D^{20}$ |
|---|---|
| Methyl S—acetyl-β-mercaptoisobutyrate | +50° (C = 1.20, CHCl₃) |
| S—acetyl-β-mercaptoisobutyric acid | −48° (C = 1.15, CHCl₃) |

EXAMPLE 32

*Torulopsis gropengiesseri* (IFO 0659) was inoculated in 2 liters of liquid culture medium (pH 6.0) containing 1.0% of glucose, 0.3% of malt extract, 0.3% of yeast extract and 0.5% of peptone, and aerobic culture was conducted using a minijar fermenter at 30° C. for 2 days. The pH was always maintained at 6.0 by using a pH controller. After completion of the culture, the cultured liquid was separated by centrifugation. After washing cells obtained (4.0 g in dry basis) with ion-exchange water, cells were suspended in 1800 ml of ion-exchange water. To this cell suspension was added 40 ml of (±) methyl S-acetyl-β-mercaptoisobutyrate, and the mixture was allowed to react by stirring at 30° C. for 30 hours. During the reaction, pH was maintained at 7.0 with 10% NaOH solution. Methyl S-acetyl-β-mercaptoisobutyrate in the reaction liquid was extracted with ethyl acetate.

The extract was distilled under reduced pressure to obtain 17.8 g of purified methyl S-acetyl-β-mercaptoisobutyrate (boiling point: 83°–85° C./3–3.5 mmHg). The optical rotatory power of this purified material was measured and found to be $[\alpha]_D^{25} = +45.0°$ (c=2.0 chloroform).

EXAMPLE 33

*Bacillus subtilis var niger* (IFO 3108) was inoculated in 2 liters of liquid culture medium (pH 7.0) containing 1.0% of meat extract, 1.0% of peptone and 0.5% of NaCl, and aerobic culture was conducted using a minijar fermenter at 30° C. for 1 day. In the same manner as in Example 32, 6.2 g of washed cells were prepared, the reaction was conducted similarly, the extraction was conducted with ethyl acetate, and the extract was distilled to obtain 17.9 g of methyl S-acetyl-β-mercaptoisobutyrate having $[\alpha]_D^{25} = -42.8°$ (c=1.4 CHCl$_3$)

EXAMPLE 34

*Pseudomonas fluorescens* (IFO 3081) was inoculated in 2 liters of the same liquid culture medium (pH 7.0) as that in Example 33, and aerobic culture was conducted using a minijar fermenter at 25° C. for 1 day. In the same manner as in Example 32, 4.2 g of washed cells were prepared, the reaction was conducted similarly, the extraction was conducted with ethyl acetate, and the extract was distilled to obtain 19.1 g of methyl S-acetyl-β-mercaptoisobutyrate having $[\alpha]_D^{25} = +46.2°$ (c=4.21, CHCl$_3$).

EXAMPLE 35

To 1.0 liter of M/2 phosphate buffer solution (pH 7.0) was added 10.0 g of Lipase M-AP 10 (manufactured by Amano Pharmaceutical Co.). To this mixture was further added 20 ml of (±) methyl S-acetyl-β-mercaptoisobutyrate. The final mixture was allowed to react by stirring at 30° C. for 40 hours. After adjusting pH of the reaction liquid to 7.0 with 10% NaOH solution, extraction was conducted once with equal volume of ethyl acetate. The extract was distilled under reduced pressure to obtain 8.7 g of methyl S-acetyl-β-mercaptoisobutyrate having $[\alpha]_D^{25} = +40.2°$ (c=1.9 CHCl$_3$).

EXAMPLES 36–53

A strain shown in Table 6 was inoculated in the same liquid culture medium as that in Example 32 or 33, and shaking culture was conducted at 30° C. for 1–3 days. Cells were separated from this cultured liquid. After sufficiently washing with ion-exchange water, cells were suspended in 500 ml of M/2 phosphate buffer solution containing 10 ml of (±) methyl S-acetyl-β-mercaptoisobutyrate. The reaction was conducted at 30° C. for 24 hours. After adjusting pH of the reaction liquid to 7.0, methyl S-acetyl-β-mercaptoisobutyrate was extracted with equal volume of ethyl acetate.

The optical rotatory power at a wave length of 589.3 mm was measured with an optical rotatory meter (digital automatic optical rotatory meter, type PM 101, manufactured by Union Giken Co.) to obtain the results shown in Table 6. From these results, it was estimated that strains shown in Table 6 produced optically active methyl S-acetyl-β-mercaptoisobutyrate having either (+) or (−) optical rotation.

TABLE 6

| Example No. | Name of strain | Optical rotation of methyl S—acetyl-β-mercapto-isobutyrate |
|---|---|---|
| 36 | *Aspergillus sojae* IAM 2703 | + |
| 37 | *Candida rugosa* IFO 0750 | − |
| 38 | *Candida parapsilosis* IFO 0708 | + |
| 39 | *Candida utilis* IFO 0396 | − |
| 40 | *Botrytio cinerea* IAM 5126 | − |
| 41 | *Ophiobolus miyabeanus* IAM 8053 | − |
| 42 | *Chaotomium semispirale* IFO 8363 | − |
| 43 | *Cladosporium resinae f. avellaneum* HUT 5050 | − |
| 44 | *Pseudomonas ovalis* IAM 1049 | + |
| 45 | *Pseudomonas putida* IFO 12996 | + |
| 46 | *Alcaligenes faecalis* IFO 13111 | − |
| 47 | *Escherichia coli* IFO 13500 | − |
| 48 | *Staphylococcus aureus* IFO 12732 | − |
| 49 | *Streptomyces griseus* IFO 3355 | − |
| 50 | *Nocardia erythropolis* IFO 12538 | − |
| 51 | *Nocardia asteroides* IFO 3384 | − |
| 52 | *Mycobacterium phlei* IFO 13160 | − |
| 53 | *Streptomyces clavuligerus* IFO 13307 | − |

EXAMPLES 54–57

To 50 ml of M/10 phosphate buffer solution (pH 7) was added 100 mg of enzyme shown in Table 7. To this mixture was added 1.0 ml of (±) methyl S-acetyl-β-mercaptoisobutyrate, and shaking culture was conducted at 30° C. for 24 hours. After adjusting pH of the reaction liquid to 7.0, extraction was conducted with equal volume of ethyl acetate. The optical rotatory power of the extract was measured in the same manner as in Examples 36–53 to obtain the results shown in Table 7. From these results, it was estimated that optically active methyl S-acetyl-β-mercaptoisobutyrate was produced.

TABLE 7

| Example No. | Enzyme (origin) | Optical rotation of methyl S—acetyl-β-mercapto-isobutyrate |
|---|---|---|
| 54 | α-chymotrypsin (pig pancreas) (Nagase Seikagaku Co.) | − |

TABLE 7-continued

| Example No. | Enzyme (origin) | Optical rotation of methyl S—acetyl-β-mercapto-isobutyrate |
|---|---|---|
| 55 | esterate (pig liver) (Sigma Co.) | — |
| 56 | lipase (Candida cylindracea) (Sigma Co.) | — |
| 57 | Pancreatin (pig pancreas) (Nakarai Chemical Co.) | |

We claim:

1. A process for preparing an optically active carboxylic acid represented by the formula (I):

$$R_1-COS-(CH_2)_n-\underset{\underset{R_2}{|}}{CH}-COOH \quad (I)$$

wherein $R_1$ is $C_{1-6}$ alkyl, benzyl or phenyl; $R_2$ is $C_{1-6}$ alkyl group; and n is 1 or 2, which comprises allowing a source containing an enzyme or microorganism capable of asymmetrically hydrolyzing an ester bond to act on an ester represented by the formula (II):

$$R_1-COS-(CH_2)_n-\underset{\underset{R_2}{|}}{CH}-COO-R_3 \quad (II)$$

wherein $R_1$, $R_2$ and n have the same meanings as those mentioned above; and $R_3$ is $C_{1-6}$ alkyl group, said source being selected from an enzyme, cultured liquid and cells or treated cells of microoganisms.

2. A process for preparing either a d-form of l-form optically active carboxylic acid ester represented by the formula (II):

$$R_1-COS-(CH_2)_n-\underset{\underset{R_2}{|}}{CH}-COOR_3 \quad (II)$$

wherein $R_1$ is $C_{1-6}$ alkyl, benzyl or phenyl; $R_2$ is $C_{1-6}$ alkyl group; and n is 1 or 2, with or without the antipode acid thereof, which comprises allowing a source containing an enzyme or microorganism capable of rearranging with or without asymmetrically hydrolyzing an ester bond to act on a carboxylic acid ester represented by the formula (II):

$$R_1-COS-(CH_2)_n-\underset{\underset{R_2}{|}}{CH}-COOR_3 \quad (II)$$

wherein $R_1$, $R_2$ and n are the same as those defined above and $R_3$ is $C_{1-6}$ alkyl group, said source being selected from an enzyme, cultured liquid and cells or treated cells of microorganisms.

3. A process according to claim 1 or 2, wherein the enzymes are lipase, esterase, α-chymotrypsin or pancreatin.

4. A process according to claim 1 or 2, wherein the microorganisms are yeasts selected from Torulopsis, Rhodotorula, Candida or Saccharomyces.

5. A process according to claim 1 or 2, wherein the microorganisms are fungi selected from such Mucor, Rhizopus, Aspergillus, Trichoderma, Penicillium, Botrytis, Chaetomium, Cladosporium or Ophiobolus.

6. A process according to claim 1 or 2, wherein the microorganisms are bacteria selected from Bacillus, Pseudomonas, Escherichia, Staphylococcus, Alcaligenes, Brevibacterium, Enterobacter, Chromobacterium, Arthrobacter, Microbacterium or Agrobacterium.

7. A process according to claim 1 or 2, wherein the microorganisms are Actinomycetes selected from Mycobacterium, Nocardia or Streptomyces.

* * * * *